US012636131B2

(12) United States Patent
Lipnik et al.

(10) Patent No.: US 12,636,131 B2
(45) Date of Patent: May 26, 2026

(54) METHOD AND SYSTEM FOR PERFORMING DENTAL SCAN

(71) Applicant: GET-GRIN INC., Airmont, NY (US)

(72) Inventors: Alon Luis Lipnik, Tel Aviv (IL); Adam Benjamin Schulhof, New City, NY (US); Yarden Eilat-Bloch, Haifa (IL); Oded Krams, Tel Aviv (IL); Pamela Sharon Oren-Artzi, Airmont, NY (US); Carmi Raz, Gizo (IL)

(73) Assignee: GET-GRIN INC., Airmont, NY (US)

( * ) Notice: Subject to any disclaimer, the term of this patent is extended or adjusted under 35 U.S.C. 154(b) by 41 days.

(21) Appl. No.: 18/397,182

(22) Filed: Dec. 27, 2023

(65) Prior Publication Data

US 2024/0315812 A1     Sep. 26, 2024

Related U.S. Application Data

(63) Continuation of application No. PCT/US2022/035176, filed on Jun. 27, 2022.
(Continued)

(51) Int. Cl.
*A61C 9/00*     (2006.01)
*A61C 7/00*     (2006.01)
*G16H 40/67*     (2018.01)

(52) U.S. Cl.
CPC ............ *A61C 9/0053* (2013.01); *A61C 7/002* (2013.01); *G16H 40/67* (2018.01)

(58) Field of Classification Search
CPC ..... A61C 9/0053; A61C 1/0088; A61C 1/002; A61C 1/0046; G16H 40/67
(Continued)

(56) References Cited

U.S. PATENT DOCUMENTS 4,611,288 A     9/1986   Duret et al.
6,402,707 B1     6/2002   Ernst, II et al.
(Continued)

FOREIGN PATENT DOCUMENTS

CN     106821287 A     6/2017
IN     202231060594 A     11/2022
(Continued)

OTHER PUBLICATIONS

PCT/US2024/013865 International Search Report and Written Opinion dated Aug. 6, 2024.
(Continued)

*Primary Examiner* — Edwyn Labaze
(74) *Attorney, Agent, or Firm* — Wilson Sonsini Goodrich & Rosati

(57) ABSTRACT

The present disclosure provides methods and systems for performing dental scans, including a method for performing a dental scan, comprising: (i) providing an intraoral adapter comprising: a viewing channel located between a proximal portion and a distal portion of an elongated housing and a mounting mechanism provided on the distal portion of the elongated housing, wherein the mounting mechanism is configured to couple the intraoral adapter to a mobile device, wherein the mobile device comprises: (a) a camera configured to capture videos or images, (b) at least one orientation sensor or at least one motion sensor, and (c) a processing unit configured to (1) process orientation or motion sensors data, and (2) process a plurality of videos or images; (ii) providing a feedback device; (iii) coupling the intraoral adapter to the mobile device; and (iv) performing a dental scan, wherein the feedback device connected to the mobile device generates a dental scan output based on one or more dental scan properties and provides the dental scan output to the user.

15 Claims, 8 Drawing Sheets

Related U.S. Application Data

(60) Provisional application No. 63/350,204, filed on Jun. 8, 2022, provisional application No. 63/215,544, filed on Jun. 28, 2021.

(58) Field of Classification Search
USPC ................................. 362/572, 573, 551, 804
See application file for complete search history.

(56) References Cited

U.S. PATENT DOCUMENTS

| | | | |
|---|---|---|---|
| 7,156,655 | B2 | 1/2007 | Sachdeva et al. |
| 7,717,708 | B2 | 5/2010 | Sachdeva et al. |
| 7,880,751 | B2 | 2/2011 | Kuo et al. |
| 9,421,074 | B2 | 8/2016 | Sachdeva et al. |
| 10,123,706 | B2 | 11/2018 | Elbaz et al. |
| 10,130,244 | B2 | 11/2018 | Patel et al. |
| 10,755,409 | B2 | 8/2020 | Salah et al. |
| 10,849,723 | B1 | 12/2020 | Yancey et al. |
| 11,096,587 | B2 | 8/2021 | Binkowski |
| 11,109,947 | B2 | 9/2021 | Adamson et al. |
| 11,392,210 | B2 | 7/2022 | Sabina et al. |
| 11,589,957 | B2 | 2/2023 | Carrier, Jr. et al. |
| 11,633,260 | B1 | 4/2023 | Amelon et al. |
| 11,638,636 | B2 | 5/2023 | Oren-Artzi et al. |
| 11,842,437 | B2 | 12/2023 | Dibra et al. |
| 12,036,085 | B2 | 7/2024 | Oren-Artzi et al. |
| 12,491,058 | B2 | 12/2025 | Pesach et al. |
| 12,527,647 | B2 | 1/2026 | Chen et al. |
| 2007/0134613 | A1 | 6/2007 | Kuo et al. |
| 2008/0172386 | A1 | 7/2008 | Ammar et al. |
| 2008/0286712 | A1 | 11/2008 | Imgrund et al. |
| 2009/0076321 | A1 | 3/2009 | Suyama et al. |
| 2013/0209954 | A1 | 8/2013 | Prakash et al. |
| 2013/0218530 | A1 | 8/2013 | Deichmann et al. |
| 2013/0286174 | A1 | 10/2013 | Urakabe et al. |
| 2014/0011162 | A1 | 1/2014 | Zegarelli |
| 2014/0272764 | A1 | 9/2014 | Miller et al. |
| 2016/0151026 | A1 | 6/2016 | Shibasaki et al. |
| 2016/0373155 | A1 | 12/2016 | O'Neill et al. |
| 2017/0071706 | A1 | 3/2017 | Lee et al. |
| 2017/0103569 | A1 | 4/2017 | Wu et al. |
| 2017/0128173 | A1 | 5/2017 | Berner et al. |
| 2018/0028294 | A1 | 2/2018 | Azernikov et al. |
| 2018/0153485 | A1 | 6/2018 | Rahmes et al. |
| 2018/0228359 | A1 | 8/2018 | Meyer et al. |
| 2018/0263730 | A1 | 9/2018 | Sirovskiy et al. |
| 2018/0303331 | A1 | 10/2018 | Salah et al. |
| 2018/0368943 | A1 | 12/2018 | Katzman et al. |
| 2019/0076026 | A1 | 3/2019 | Elbaz et al. |
| 2019/0167115 | A1 | 6/2019 | Dorodvand et al. |
| 2019/0200903 | A1 | 7/2019 | Watson |
| 2019/0254790 | A1 | 8/2019 | Lancelle et al. |
| 2019/0269482 | A1 | 9/2019 | Shanjani et al. |
| 2019/0313963 | A1 | 10/2019 | Hillen |
| 2019/0328489 | A1 | 10/2019 | Capron-Richard et al. |
| 2019/0350680 | A1 | 11/2019 | Chekh et al. |
| 2020/0000551 | A1 | 1/2020 | Li et al. |
| 2020/0000562 | A1 | 1/2020 | Wey |
| 2020/0085546 | A1 | 3/2020 | Li et al. |
| 2020/0107915 | A1 | 4/2020 | Roschin et al. |
| 2020/0138518 | A1 | 5/2020 | Lang |
| 2020/0143541 | A1 | 5/2020 | Wang et al. |
| 2020/0146646 | A1 | 5/2020 | Tuzoff et al. |
| 2020/0155276 | A1* | 5/2020 | Cam .................... A61N 1/0548 |
| 2020/0214801 | A1 | 7/2020 | Wang et al. |
| 2020/0305808 | A1 | 10/2020 | Ezhov et al. |
| 2020/0349356 | A1 | 11/2020 | Matias et al. |
| 2020/0359777 | A1* | 11/2020 | Pesach ................. G06V 40/165 |
| 2020/0390521 | A1 | 12/2020 | Kopelman et al. |
| 2020/0404243 | A1 | 12/2020 | Saphier et al. |
| 2021/0220086 | A1 | 7/2021 | German |
| 2021/0282634 | A1 | 9/2021 | Oren-Artzi et al. |
| 2021/0353152 | A1 | 11/2021 | Saphier et al. |
| 2021/0377374 | A1 | 12/2021 | Peterson et al. |
| 2022/0030162 | A1 | 1/2022 | Cramer et al. |
| 2022/0165388 | A1 | 5/2022 | Chernov et al. |
| 2022/0222910 | A1 | 7/2022 | Salah et al. |
| 2022/0338723 | A1 | 10/2022 | Farkash et al. |
| 2022/0395361 | A1 | 12/2022 | Zegarelli et al. |
| 2022/0415476 | A1 | 12/2022 | Connor |
| 2023/0111070 | A1 | 4/2023 | Xia et al. |
| 2023/0141733 | A1 | 5/2023 | Kopelman et al. |
| 2023/0149135 | A1 | 5/2023 | Lipnik et al. |
| 2023/0346531 | A1 | 11/2023 | Oren-Artzi et al. |
| 2024/0008731 | A1 | 1/2024 | Meyer et al. |
| 2024/0164874 | A1 | 5/2024 | Lipnik et al. |
| 2024/0164875 | A1 | 5/2024 | Raz et al. |
| 2025/0072757 | A1 | 3/2025 | Elbaz et al. |
| 2025/0143841 | A1 | 5/2025 | Oren-Artzi et al. |
| 2025/0311928 | A1 | 10/2025 | Lipnik et al. |
| 2026/0017794 | A1 | 1/2026 | Lipnik et al. |
| 2026/0030855 | A1 | 1/2026 | Anderson et al. |

FOREIGN PATENT DOCUMENTS

| | | | |
|---|---|---|---|
| KR | 101583547 | B1 | 1/2016 |
| WO | WO-2005008441 | A2 | 1/2005 |
| WO | WO-2016142817 | A1 | 9/2016 |
| WO | WO-2018085718 | A2 | 5/2018 |
| WO | WO-2019215129 | A1 | 11/2019 |
| WO | WO-2021130582 | A1 | 7/2021 |
| WO | WO-2021224929 | A1 | 11/2021 |
| WO | WO-2021236616 | A1 | 11/2021 |
| WO | WO-2022020267 | A1 | 1/2022 |
| WO | WO-2023278354 | A1 | 1/2023 |
| WO | WO-2023009763 | A1 | 2/2023 |
| WO | WO-2023009764 | A1 | 2/2023 |
| WO | WO-2023009859 | A2 | 2/2023 |
| WO | WO-2023009859 | A3 | 3/2023 |
| WO | WO-2024138003 | A1 | 6/2024 |
| WO | WO-2024163674 | A2 | 8/2024 |
| WO | WO-2024163674 | A3 | 10/2024 |
| WO | WO-2024206944 | A2 | 10/2024 |
| WO | WO-2024243437 | A2 | 11/2024 |
| WO | WO-2025034760 | A1 | 2/2025 |
| WO | WO-2024206944 | A3 | 3/2025 |
| WO | WO-2024243437 | A3 | 4/2025 |

OTHER PUBLICATIONS

PCT/US2024/022399 International Search Report and Written Opinion dated Sep. 18, 2024.

PCT/US2024/022399 Invitation to Pay Additional Fees dated Jun. 26, 2024.

PCT/US2024/030836 International Search Report and Written Opinion dated Oct. 1, 2024.

PCT/US2024/041133 International Search Report and Written Opinion dated Jan. 8, 2025.

PCT/US2024/041133 Invitation to Pay Additional Fees dated Oct. 21, 2024.

U.S. Appl. No. 18/157,280 Office Action dated Mar. 20, 2025.

U.S. Appl. No. 18/735,060 Office Action dated Mar. 21, 2025.

Co-pending U.S. Appl. No. 18/735,060, inventors Oren-Artzi; Pamela Sharon et al., filed Jun. 5, 2024.

El Kattan et al. A New Horizontal Plane of the Head. Open Access Maced J Med Sci. May 20, 2018; 6(5):767-771. Retrieved Mar. 1, 2023 at URL: https://oamjms.eu/index.php/mjms/article/view/oamjms.2018.172/2103.

EP21846558.1 Extended European Search Report dated Jul. 2, 2024.

EP21809886.1 Extended European Search Report dated May 8, 2024.

PCT/US2021/032932 International Search Report and Written Opinion dated Sep. 9, 2021.

PCT/US2021/042247 International Search Report and Written Opinion dated Nov. 3, 2021.

PCT/US2022/035176 International Search Report and Written Opinion dated Sep. 15, 2022.

PCT/US2022/038737 International Search Report and Written Opinion dated Dec. 19, 2022.

(56)         References Cited

OTHER PUBLICATIONS

PCT/US2022/038943 International Search Report and Written Opinion dated Feb. 16, 2023.
PCT/US2023/085455 International Search Report and Written Opinion dated Apr. 2, 2024.
PCT/US2024/013865 Invitation to Pay Additional Fees dated May 28, 2024.
Prados-Privado et al. A Convolutional Neural Network for Automatic Tooth Numbering in Panoramic Images. BioMed Research International, vol. 2021, Article ID 3625386, 7 pages. Published Dec. 14, 2021.
Tamayo-Quintero, J. D. et al. Image Segmentation Techniques Applied to Point Clouds of Dental Models with an Improvement in Semi-Automatic Teeth Segmentation. Proceedings of the International Conference on Image Processing, Computer Vision, and Pattern Recognition (IPCV): 1-7 (2014). Retrieved at URL: http://world-comp.org/preproc2014/IPC2502.pdf.
U.S. Appl. No. 18/057,095 Notice of Allowance dated Apr. 22, 2024.
U.S. Appl. No. 18/057,095 Notice of Allowance dated Jun. 21, 2024.
U.S. Appl. No. 18/057,095 Notice of Allowance dated Mar. 27, 2024.
U.S. Appl. No. 18/057,095 Office Action dated Sep. 14, 2023.
AU2021277220 Office Action dated Dec. 11, 2025.
CA3179459 Office Action dated Jan. 23, 2026.

Co-pending U.S. Appl. No. 19/397,135, inventor Eilat-Bloch; Yarden, filed Nov. 21, 2025.
Co-pending U.S. Appl. No. 19/531,570, inventors Lipnik; Alon Luis et al., filed Feb. 5, 2026.
Co-pending U.S. Appl. No. 30/022,767, inventors Eilat-Bloch; Yarden et al., filed Sep. 11, 2025.
EP22834011.3 Extended European Search Report dated Apr. 7, 2025.
EP22850341.3 Extended European Search Report dated Apr. 30, 2025.
EP22850389.2 Extended European Search Report dated Jun. 16, 2025.
EP22850389.2 Partial European Search Report dated Mar. 26, 2025.
IN202217072913 Office Action dated Nov. 3, 2025.
Morris, Ryan S. et al. Accuracy of Dental Monitoring 3D digital dental models using photograph and video mode. American journal of orthodontics and dentofacial orthopedics 156(3):420-428 (2019).
Nicole Hove, Lauren. Reliability of Dental Monitoring 3D Digital Dental Models Using Video Mode. University of Illinois at Chicago :1-159 (2018).
PCT/US2025/040975 International Search Report and Written Opinion dated Oct. 21, 2025.
PCT/US2025/048317 International Search Report and Written Opinion dated Dec. 11, 2025.
U.S. Appl. No. 18/157,280 Office Action dated Dec. 23, 2025.
U.S. Appl. No. 18/424,237 Office Action dated Feb. 9, 2026.
U.S. Appl. No. 18/735,060 Office Action dated Dec. 30, 2025.

* cited by examiner

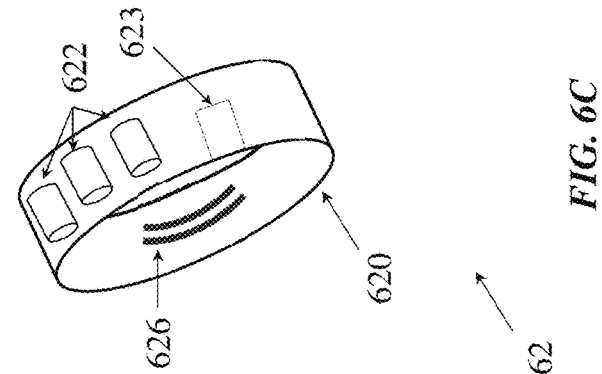
*FIG. 6C*
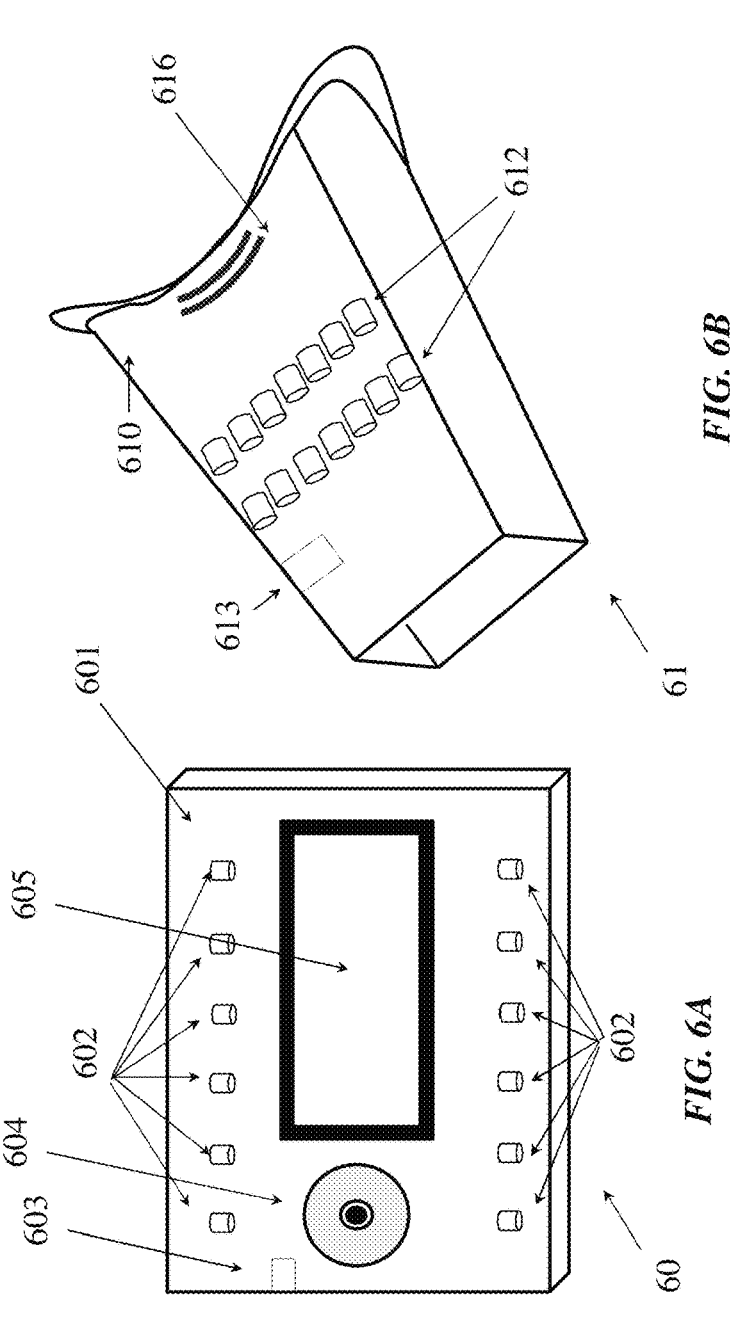
*FIG. 6B*
*FIG. 6A*

METHOD AND SYSTEM FOR PERFORMING DENTAL SCAN

CROSS REFERENCE

This application is a continuation of International Patent Application PCT/US22/35176, filed Jun. 27, 2022, which claims priority to U.S. Provisional Application No. 63/215,544, filed Jun. 28, 2021, and U.S. Provisional Application No. 63/350,204, filed Jun. 8, 2022, each of which is incorporated herein by reference in its entirety.

TECHNICAL FIELD

Methods and systems for performing intraoral dental scans are described herein.

BACKGROUND

Dental professionals and orthodontists may treat and monitor a user's dental condition based on in-person visits. Treatment and monitoring of a user's dental condition may require a user to schedule multiple in-person visits to a dentist or orthodontist. The quality of treatment and the accuracy of monitoring may vary depending on how often and how consistently a user sees a dentist or orthodontist. In some cases, suboptimal treatment outcomes may result if a user is unable or unwilling to schedule regular visits to a dentist or orthodontist.

SUMMARY

Recognized herein is a need for remote dental monitoring solutions to allow dental users to receive high quality dental care, without requiring a dental professional to be physically present with the user. Some dental professionals and orthodontists may use conventional teledentistry solutions to accommodate users' needs and schedules. However, such conventional teledentistry solutions may provide inadequate levels of supervision. Further, such conventional teledentistry solutions may be limited by an inaccurate or insufficient monitoring of a user's dental condition based on one or more photos taken by the user, if the photos do not adequately capture various intraoral features.

The present disclosure provides methods and systems for intraoral imaging with real time feedback to the user on the intraoral imaging quality to enhance remote dental monitoring capabilities. As used herein, intraoral imaging may refer to the acquisition of one or more intraoral videos and/or intraoral images. The methods and systems disclosed herein may provide a convenient solution and user experience for dental users to capture one or more intraoral videos or images using a mobile device such as a smartphone. The methods and systems disclosed herein may provide dentists and orthodontists with a detailed analysis of the user's dental condition based on one or more intraoral images or videos, including full arch scans, captured remotely by the user. In an aspect, described herein, is a method for performing a dental scan, comprising: (i) providing an intraoral adapter comprising: a viewing channel located between a proximal portion and a distal portion of an elongated housing and a mounting mechanism provided on the distal portion of the elongated housing, wherein the mounting mechanism is configured to couple the intraoral adapter to a mobile device, wherein the mobile device comprises: (a) a camera configured to capture videos or images, (b) at least one orientation sensor or at least one motion sensor, and (c) a processing unit configured to (1) process orientation or motion sensors data, and (2) process a plurality of videos or images; (ii) providing a feedback device; (iii) coupling the intraoral adapter to the mobile device; and (iv) performing a dental scan, wherein the feedback device connected to the mobile device generates a dental scan output based on one or more dental scan properties and provides the dental scan output to the user.

In some embodiments, the mobile device is a mobile smartphone. In some embodiments, the feedback device comprises a speaker, and wherein the dental scan output comprises an audio output. In some embodiments, the audio output comprises a sound, a message, or a voice. In some embodiments, the feedback device comprises a mechanical device, and wherein the dental scan output comprises a vibration, a tremble, a sound, a temperature, an electric current, a stab, or a pinch. In some embodiments, the feedback device comprises a light source, and wherein the dental scan output comprises light. In some embodiments, the feedback device comprises a screen, and wherein the dental scan output comprises a shape, a message, or light showing on the screen. In some embodiments, the feedback device is connected by a wired or wireless port, and wherein the feedback device is connected to said mobile device via said connection.

In some embodiments, the dental scan properties comprise at least one of: distance, direction, angle, focus, light condition, location, movement speed, motion blur, acceleration, shiver, time, tooth appearance, predetermined scan order, predetermined scan sites, dental scan properties provided by a scan administrator, specific module use, intraoral adapter coupling, or placement. In some embodiments, the scan administrator is a dentist, orthodontist, dental hygienist, dental assistant, or other dental health professional. In some embodiments, the dental scan properties further comprise videos or images. In some embodiments, the videos or images are associated with one or more of: specific tooth, specific tooth angle, aligner appearance, and reference aid. In some embodiments, the dental scan output alerts a user when one or more dental scan properties are not met during the dental scan. In some embodiments, the dental scan output alerts a user when one or more dental scan properties are met during the dental scan. In some embodiments, the dental scan output is generated while performing the dental scan. In some embodiments, the feedback device generates the dental scan output while performing the dental scan and upon reaching at least one of the dental scan properties.

In some embodiments, the performed dental scan is monitored at a dispatch location while performing the dental scan, and wherein the feedback device is configured to be activated from the dispatch location to generate an output. In some embodiments, the dispatch location is a location that is separate from a location where the dental scan is performed. In some embodiments, the output comprises one or more dental scan properties, and wherein the output is generated by a scan administrator. In some embodiments, the scan administrator is a dentist, orthodontist, dental hygienist, dental assistant, or other dental health professional. In some embodiments, the orientation or motion sensors data is stored and added to the dental scan output. In some embodiments, the feedback device output comprises a video.

In an aspect, described herein is a dental scan feedback device, comprising a wired or wireless connection to a mobile device and configured to generate one or more outputs selected from a group consisting of a speaker, a mechanical device, a light source, and a screen. In some embodiments, the feedback device is located on the mobile device during a dental scan. In some embodiments, the feedback device is located on an intraoral adapter during a dental scan. In some embodiments, the feedback device is configured to be worn by a user performing a dental scan during the dental scan.

In an aspect, described herein is a dental scan system, comprising: an intraoral adapter, a smartphone comprising a camera, and software comprising dental scan properties, wherein the smartphone activates one or more features at the start, during, or at the end of an intraoral capture video to achieve one or more dental scan properties. In some embodiments, the intraoral adapter comprises: a viewing channel located between a proximal portion and a distal portion of an elongated housing and a mounting mechanism provided on the distal portion of the elongated housing, wherein the mounting mechanism is configured to couple the intraoral adapter to the smartphone. In some embodiments, the one or more smartphone features comprise a speaker, a light bulb, a screen, or a vibration. In some embodiments, the software monitors video capture of the smartphone camera and compares at least one of the dental scan properties to the video capture.

As used herein, the term "dental scan" refers to a process that generates a video or an image frame from a video capture of the intraoral perspective of the teeth arch or of a tooth.

As used herein, the term "dental scan properties" refers to one or more parameters that can be modified or optimized to enhance the quality of a dental scan.

Unless otherwise defined, all technical and scientific terms used herein have the same meaning as commonly understood by one of ordinary skill in the art. Although suitable methods and materials are described below, methods and materials similar or equivalent to those described herein can be used in the practice of the systems and methods described herein. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the methods and systems described herein involves performing or completing selected tasks or steps manually, automatically, or a combination thereof.

Moreover, according to actual instrumentation and equipment of preferred embodiments of methods, apparatus and systems described herein, several selected steps could be implemented by hardware or by software on any operating system of any firmware or a combination thereof. For example, as hardware, selected steps of the systems and methods described herein could be implemented as a chip or a circuit. As software, selected steps of the systems and methods described herein could be implemented as a plurality of software instructions being executed by a computer using any suitable operating system. In any case, selected steps of the systems and methods described herein could be described as being performed by a data processor, such as a computing platform for executing a plurality of instructions.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

In order to understand the systems and methods described herein and to see how they may be carried out in practice, embodiments will now be described, by way of non-limiting example only, with reference to the accompanying figures. In the figures, identical and similar structures, devices or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIGS. 6A, 6B, 6C schematically illustrate an exemplary dental scan feedback device, in accordance with some embodiments.

DETAILED DESCRIPTION

Figure 1:
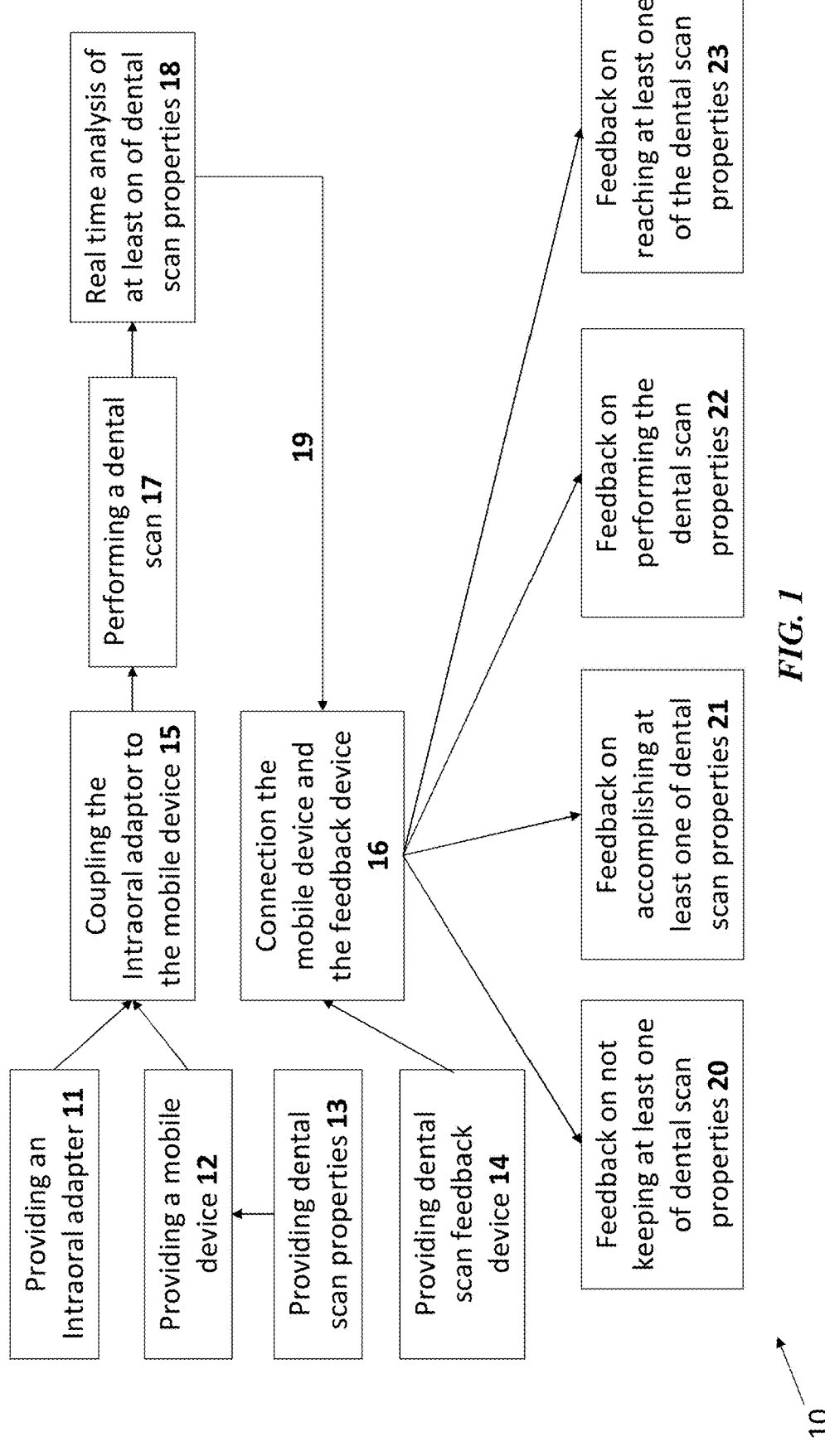
FIG. 1 schematically illustrates a method for capturing intraoral videos or images, in accordance with some embodiments.

While various embodiments have been shown and described herein, it will be obvious to those skilled in the art that such embodiments are provided by way of example only. Numerous variations, changes, and substitutions may occur to those skilled in the art without departing from the systems and methods described herein. It should be understood that various alternatives to the embodiments described herein may be employed.

The term "real-time," as used herein, generally refers to a simultaneous or substantially simultaneous occurrence of a first event or action with respect to an occurrence of a second event or action. In some embodiments, a real-time action or event may be performed within a response time of about 0.001 seconds to about 10 seconds. In some embodiments, a real-time action or event may be performed within a response time of about 0.001 seconds to about 0.01 seconds, about 0.001 seconds to about 0.1 seconds, about 0.001 seconds to about 1 second, about 0.001 seconds to about 5 seconds, about 0.001 seconds to about 10 seconds, about 0.01 seconds to about 0.1 seconds, about 0.01 seconds to about 1 second, about 0.01 seconds to about 5 seconds, about 0.01 seconds to about 10 seconds, about 0.1 seconds to about 1 second, about 0.1 seconds to about 5 seconds, about 0.1 seconds to about 10 seconds, about 1 second to about 5 seconds, about 1 second to about 10 seconds, or about 5 seconds to about 10 seconds. In some embodiments, a real-time action or event may be performed within a response time of about 0.001 seconds, about 0.01 seconds, about 0.1 seconds, about 1 second, about 5 seconds, or about 10 seconds. In some embodiments, a real-time action or event may be performed within a response time of at least about 0.001 seconds, about 0.01 seconds, about 0.1 seconds, about 1 second, or about 5 seconds. In some embodiments, a real-time action or event may be performed within a response time of at most about 0.01 seconds, about 0.1 seconds, about 1 second, about 5 seconds, or about 10 seconds. A real-time action may be performed by one or more computer processors.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "a," "an," and "the," as used herein, generally refer to singular and plural references unless the context clearly dictates otherwise.

Overview

In an aspect, the present disclosure provides methods and systems for intraoral imaging with real time feedback to the user on the intraoral imaging process quality, to enhance remote dental monitoring capabilities. As used herein, intraoral imaging may refer to the acquisition of one or more intraoral videos and/or intraoral images with a mobile device coupled to an intraoral adapter. The methods and systems disclosed herein may provide a convenient solution and user experience for dental users to capture one or more intraoral videos or images using a mobile device such as a smartphone. The methods and systems disclosed herein may provide dentists and orthodontists with a detailed analysis of the user's dental condition based on one or more full arch scans captured remotely by the user.

The methods and systems of the present disclosure may also be used to provide dental users with an intuitive, user-friendly interface for remote dental scanning without requiring assistance from a dentist or a dental assistant. The intuitive, user-friendly interface may be provided as part of a software application. The method and system disclosed herein may permit dentists to view high quality videos or images of a user's teeth so that the dentist can monitor the user's teeth or treatment progress without being physically present and without having to provide personalized or customized instructions for how to acquire the intraoral images or videos.

In an aspect, the present disclosure provides methods and systems for a dental scan. The methods and systems of the present disclosure may be implemented using a software application that is configured to enable a dental user to capture videos and/or images of intraoral regions. The software application may be used by a user or a subject (e.g., a dental user) in conjunction with a mobile device to remotely monitor a dental anatomy or a dental condition of the subject. A dental anatomy may comprise one or more dental structures of the user, including one or more tooth structures or dental arches of the subject. The dental condition may comprise a development, a growth, a movement, an appearance, a condition, a physical arrangement, a position, and/or an orientation of the subject's teeth. In some cases, the dental condition may comprise a functional aspect of the user's teeth, such as how two or more teeth contact each other or how the teeth move over a period of time.

The dental scan may be used to enable remote dental monitoring. As used herein, remote monitoring may refer to monitoring a dental anatomy or a dental condition of a user that is performed at one or more locations remote from the user. For example, a dentist or a medical specialist may monitor the dental anatomy or dental condition in a first location that is different than a second location where the user is located. The first location and the second location may be separated by a distance spanning at least 1 meter, 1 kilometer, 10 kilometers, 100 kilometers, 1000 kilometers, or more.

The remote monitoring may be performed by assessing a dental anatomy or a dental condition of the subject using one or more dental scan captured by the subject when the user is located remotely from the dentist or a dental office. In some cases, the remote monitoring may be performed in real-time such that a dentist is able to assess the dental anatomy or the dental condition when a subject uses a mobile device to acquire one or more dental scan of one or more intraoral regions in the user's mouth. The remote monitoring may be performed using equipment, hardware, and/or software that is not physically located at a dental office.

The software application for dental scan may be configured to run on a mobile device. The mobile device may comprise a smartphone, a tablet, a laptop, or any suitable device that may be used by a user to capture one or more dental scan. The software application may be installed on a mobile device of a user undergoing a dental treatment or who will be undergoing a dental treatment. The software application may be a user-side software application.

In some cases, the user-side software application may be used in a compatible manner with a practitioner-side software application that is accessible by a caregiver. The user-side software application and the practitioner-side software application may enable real-time communication and sharing of dental scan, or data between one or more users and one or more caregivers. The one or more caregivers may comprise, for example, a dentist, an orthodontist, an oral surgeon, individuals having one or more dental specialties, or a dental staff practitioner.

Capturing Dental Scan

In an aspect, the present disclosure provides methods and systems for intraoral imaging with real-time feedback to the user on the intraoral imaging process. In an aspect, the present disclosure provides methods and systems for a dental scan comprising; providing an intraoral adapter comprising a viewing channel between a proximal portion and a distal portion of the elongated housing, and providing a mounting mechanism on the distal portion of the elongated housing, wherein the mounting mechanism is configured to couple the intraoral adapter to a mobile device; providing a mobile device comprising a camera with an ability to capture videos or images, at least one orientation sensor or at least one motion sensor, a processing unit configured to (i) process orientation or motion sensors data, and (ii) process a plurality of videos or images; providing a feedback device; providing dental scan properties; coupling the intraoral adapter to the mobile device; and, performing a dental scan wherein the feedback device generates output to the user on dental scan properties.

In some cases, the mobile device is a mobile smartphone. In some cases, the mobile device can comprise more than one camera. In some cases, the mobile device comprises a feedback device The one or more dental scans may be captured using one or more cameras of a mobile device. In some cases, the mobile device may be coupled to a compatible intraoral adapter comprising a viewing channel for capturing the one or more dental scans. The intraoral adapter may be configured to provide an imaging region for the one or more cameras of the mobile device. One or more of the user's dental features or intraoral regions may be viewable within the imaging region, which may be defined by a size and/or a shape of the intraoral adapter. In some cases, the viewing channel of the intraoral adapter may comprise a hexagonal or a polygonal rounded cross-sectional shape. Using a compatible intraoral adapter may provide multiple benefits, such as consistently defining an appropriate or suitable dental imaging region and standardizing a distance between the cameras of the user's mobile device and the one or more dental features the user wishes to image.

Figure 3:
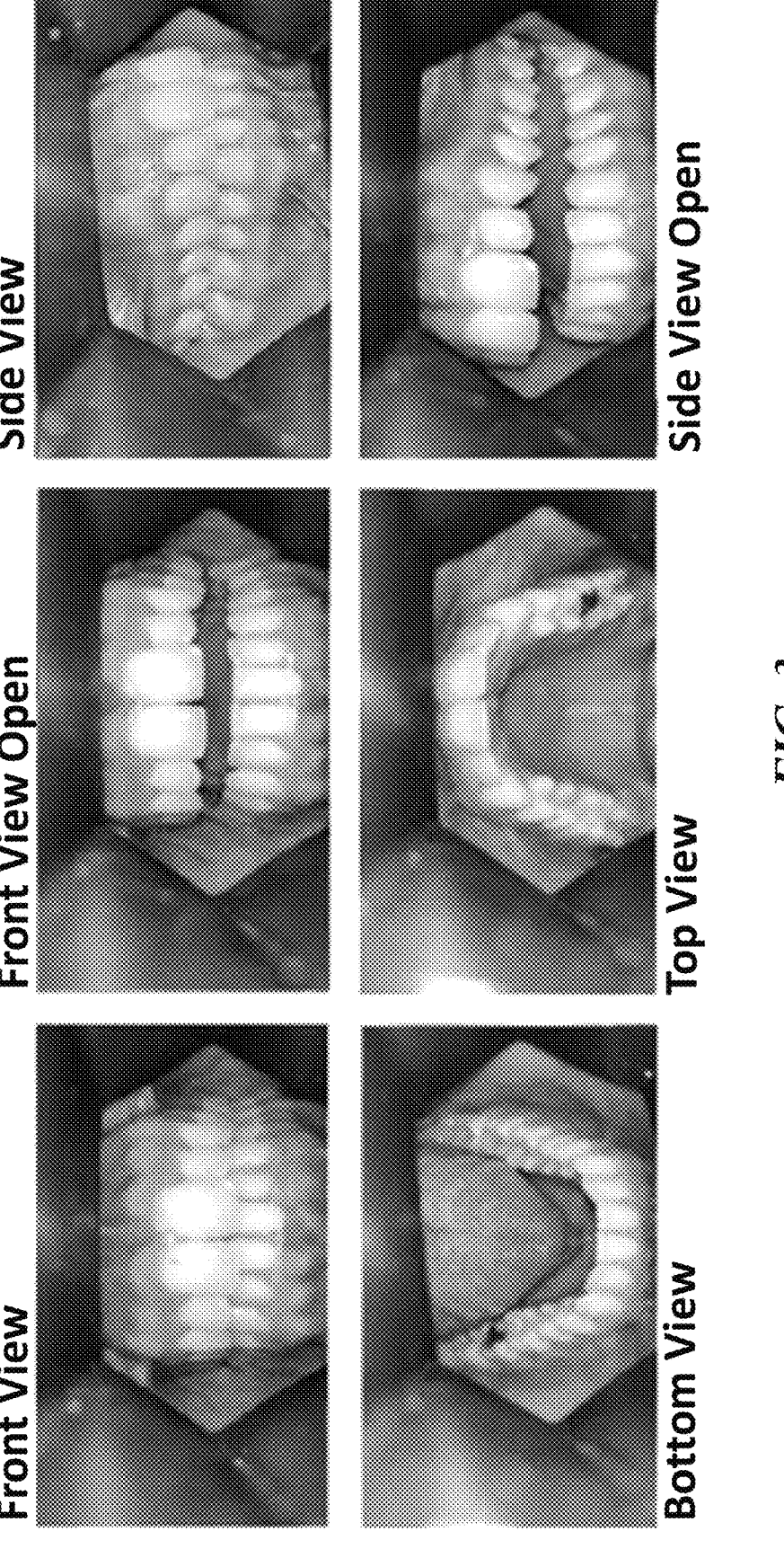
FIG. 3 schematically illustrates a plurality of intraoral images captured using the method provided herein, in accordance with some embodiments.

In some cases, the dental imaging region may comprise a shape that is configured to enable the user to capture one or more intraoral videos or intraoral images of a molar region while minimizing a movement of the mobile device and the intraoral adapter that is used to capture the one or more dental scans, so as to provide stabilization to enable consistent image alignment for processing. The shape of the dental imaging region may be a circle, an ellipse, an oval, or a polygon with three or more sides. In some cases, the dental imaging region may be in the shape of a hexagon or a rounded polygon. In such cases, the dental scans captured using the mobile device and the intraoral adapter may be framed within a hexagonal shape as shown in FIG. 3.

In some cases, the intraoral adapter may further comprise one or more sensors configured to automatically detect when a user's smartphone camera and the intraoral adapter are optically aligned to capture one or more dental scans. In some cases, the intraoral adapter may be configured to permit dynamic adjustment of lighting, illumination, brightness, contrast, and/or any other imaging conditions so that the user may take suitable dental scans using the intraoral adapter and the user's mobile device. In some cases, the intraoral adapter may be configured to permit the user to take a plurality of images with different lighting conditions or illumination conditions to reveal certain characteristics that are only apparent or visible under one or more such conditions. The plurality of images may comprise one or more bright-field images and/or one or more dark-field images. In some cases, the intraoral adapter may be configured to adjust an amount of light that is transmitted through the intraoral adapter (e.g., from a camera flash of the user's mobile device).

In some cases, at least some of the performed dental scan data is stored and referenced in a dental scan output.

In some cases, the dental scan output is a video

Dental Scan Properties

In an aspect, the present disclosure provides methods and systems for intraoral imaging with real-time feedback to the user on the intraoral imaging process in accordance with predetermined dental scan properties.

In an aspect, the present disclosure provides methods and systems for a dental scan or performing of a dental scan, comprising providing dental scan properties.

In some cases, the dental scan properties comprise desired distance data and distance margins data between the mobile device camera and the desired intraoral area while performing the dental scan.

In some cases, the dental scan properties comprise desired direction data and direction margins data between the mobile device and the desired intraoral area while performing the dental scan.

In some cases, the dental scan properties comprise desired angle data and angle margins data between the mobile device and the desired intraoral area while performing the dental scan.

In some cases, the dental scan properties comprise desired focus data and focus margins data of the mobile device camera while performing the dental scan.

In some cases, the dental scan properties comprise desired light condition data and light condition margins data while performing the dental scan. In some cases, the dental scan properties comprise desired location data while performing the dental scan. In some cases, the dental scan properties comprise desired movement speed data and movement speed margins data between the mobile device and teeth while performing the dental scan.

In some cases, the dental scan properties comprise desired motion blur data and motion blur margins data between the mobile device and the desired intraoral area while performing the dental scan. In some cases, the dental scan properties comprise desired acceleration data and acceleration margins data between the mobile device and the desired intraoral area while performing the dental scan.

In some cases, the dental scan properties comprise desired shiver data and shiver margins data between the mobile device and the desired intraoral area while performing the dental scan. In some cases, the dental scan properties comprise desired time data and time margins data for performing the dental scan.

In some cases, the dental scan properties comprise desired tooth appearance data while performing the dental scan. In some cases, the dental scan properties comprise desired predetermined scan order data while performing the dental scan.

In some cases, the dental scan properties comprise desired predetermined scan sites data while performing the dental scan. In some cases, the dental scan properties comprise specific module use data while performing the dental scan.

In some cases, the dental scan properties comprise intraoral adapter coupling and placement data while performing the dental scan.

In some cases, the dental scan properties further comprise videos or images. In some cases, the videos or images comprise aligner data acquired while performing the dental scan. In some cases, the videos or images comprise reference aid data acquired while performing the dental scan. In some cases, the videos or images comprise dental scan properties received from operator data while performing the dental scan.

Feedback

In an aspect, the present disclosure provides methods and systems for intraoral imaging with real-time feedback to the user on the intraoral imaging process. In an aspect, the present disclosure provides methods and systems for a dental scan, comprising providing a mobile device and a feedback device. In some cases, the feedback device comprise a speaker and the feedback device output is a sound, a message or a voice.

In some cases, the feedback device comprises a mechanical element. In some cases, the feedback device output is a vibration, a tremble, a sound, temperature, an electric current, a stab or a pinch In some cases, the feedback device comprises a light source. In some cases, the feedback device output is light.

In some cases, the feedback device comprises a screen. In some cases, the feedback device output is a shape, a message or light showing on the screen.

In some cases, the feedback device is connected by wired or wireless port. In some cases, the feedback device is connected to said mobile device via said connection.

In some cases, the feedback device is located on the mobile device during the dental scan. In some cases, the feedback device is an integrated device of the mobile device, such as a smartphone.

In some cases, the feedback device is located on the intraoral adapter during the dental scan. In some cases, the feedback device is an integrated device of the intraoral adapter.

In some cases, the feedback device is located on the user performing the dental scan during the dental scan. In some cases, the feedback device is a smart watch, a bracelet or any external device with a connection to the user's body.

In some cases, the feedback device generates output when performing the dental scan while not keeping at least one of the dental scan properties.

In some cases, the feedback device generates output when performing the dental scan and accomplishing at least one of the dental scan properties.

In some cases, the dental scan feedback is given while performing the dental scan. In some cases, the dental scan feedback is given simultaneously while performing the dental scan.

In some cases, the feedback device generates output while performing the dental scan on reaching at least one of the dental scan properties.

In some cases, the performed dental scan is monitored on a dispatch location while performing the dental scan. In some cases, the feedback device can be activated to generate an output from the dispatch location.

FIG. 1 illustrates an example of a method for a dental scan 10. First, an intraoral adapter 11 and a mobile device 12 with dental scan properties 13 and a dental scan feedback device 14 may be provided to a subject. Next, the subject may connect a mobile device to an intraoral adapter 15 and have the mobile device and the feedback device connect 16. Next, the subject may use the mobile device to initiate an intraoral dental scan 17. While performing the intraoral dental scan 17, at least one of the dental scan properties can be analyzed 18. The feedback device can generate output if at least one of the dental scan properties is kept during the dental scan 20. The feedback device can generate output if at least one of the dental scan properties is accomplished during the dental scan 21, The feedback device can generate output if the dental scan preforms the dental scan properties 22. The feedback device can generate output if at least one of the dental scan properties is reached 23. The dental scan process (e.g., capturing videos or images) may comprise a left to right or a right to left movement of the intraoral adapter while the subject has a closed bite. The dental scan may comprise a left to right or a right to left movement of the intraoral adapter while the subject has an open bite. The dental scan may comprise one or more scans of an upper dental arch and/or a lower dental arch of the subject.

The dental scan disclosed herein may be used with any type of device or intraoral adapter that is configured to permit capture of a user's teeth or dental structure. The intraoral adapter may be configured to permit the user to capture one or more intraoral videos or images using a mobile device or a smartphone. The intraoral adapter may be configured to position the mobile device or smartphone such that the user is able to capture the images or videos from one or more predetermined positions or viewing angles.

Figure 2A:
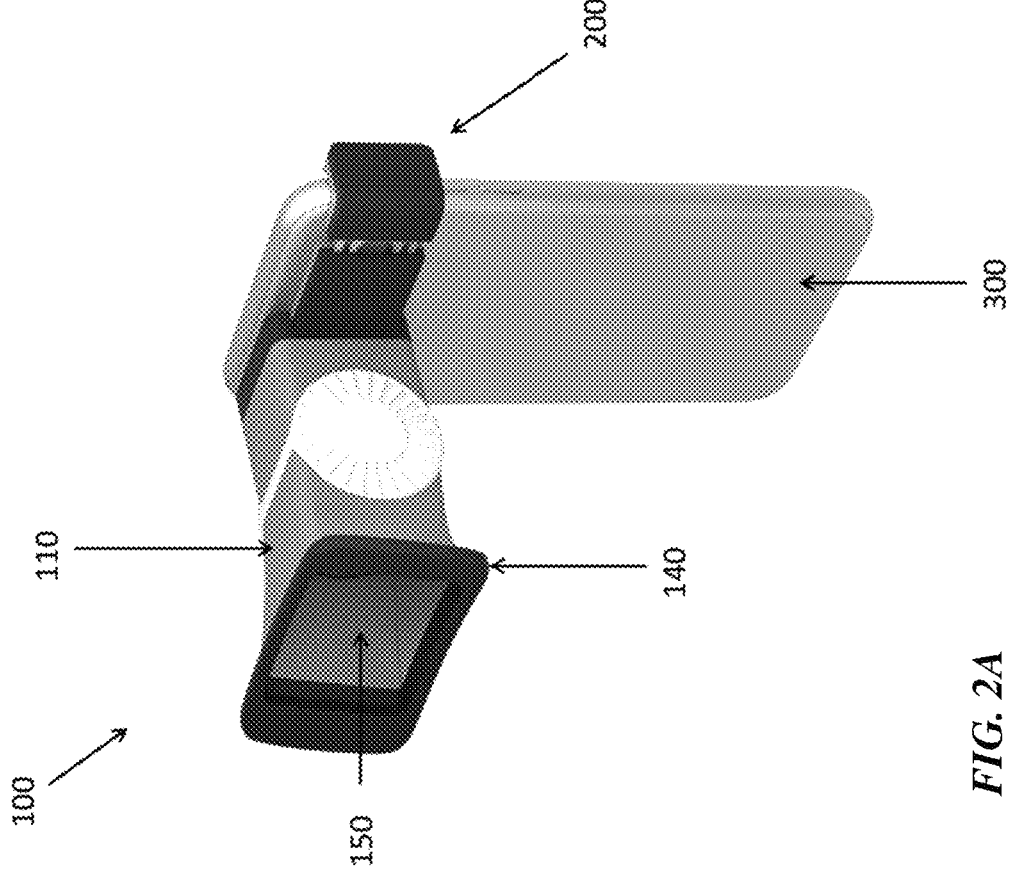
FIGS. 2A, 2B, 2C, 2D, and 2E schematically illustrate an exemplary intraoral adapter to which a mobile device can be coupled to in order to capture intraoral videos or images, in accordance with some embodiments.
Figure 2B:
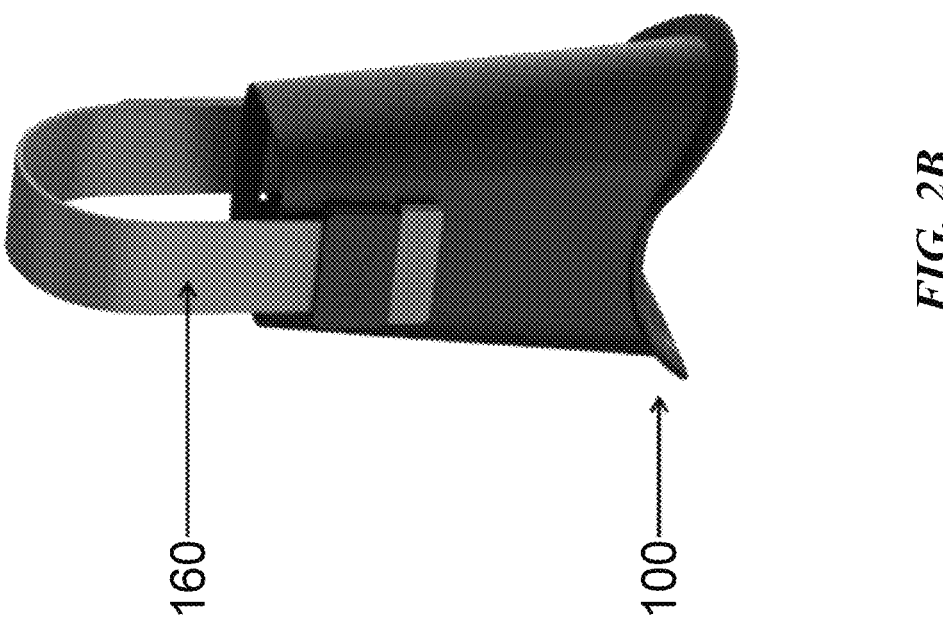
Figures 2C, 2D, 2E:
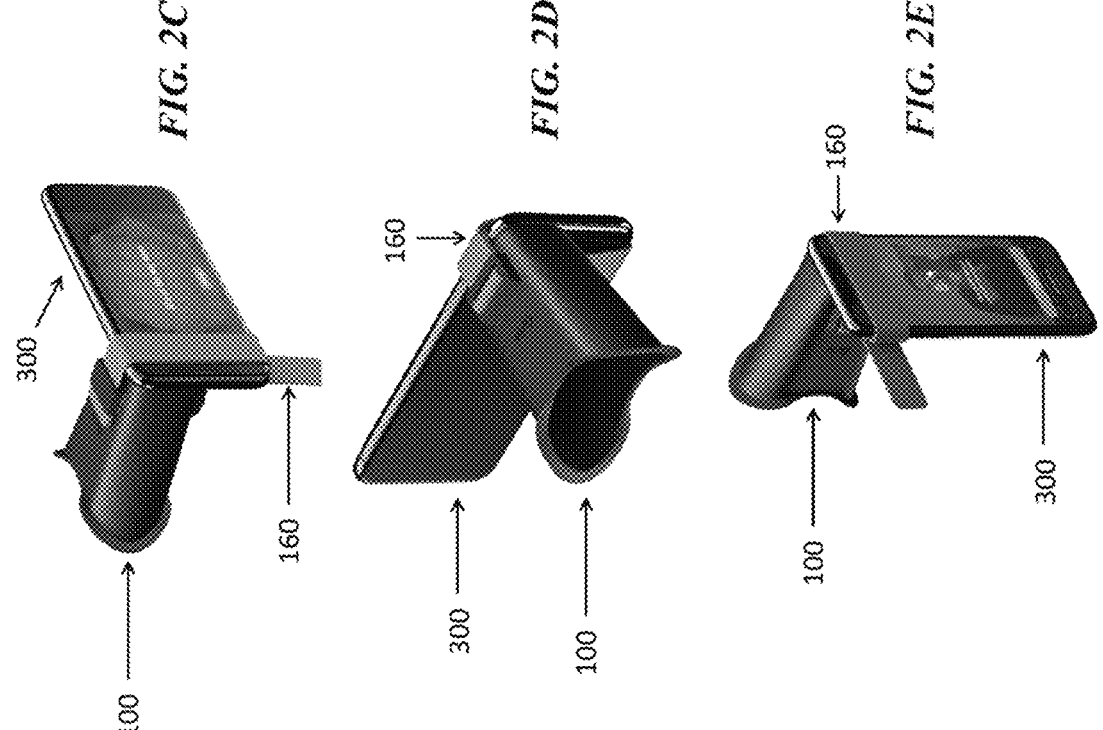

FIG. 2A illustrates an example of an intraoral adapter 100 that may be used with the systems and methods disclosed herein. The intraoral adapter 100 may comprise an elongated housing 110 with a mounting mechanism 200 and a mobile device 300 coupled to the intraoral adapter 100 via the mounting mechanism 200. The mounting mechanism 200 may be configured to couple the mobile device 300 to the intraoral adapter 100 such that a longitudinal axis of a viewing channel 150 of the intraoral adapter 100 is substantially aligned with an optical axis of one or more cameras of the mobile device 300. The mounting mechanism 200 may be configured to mechanically engage with the mobile device 300 or a casing of the mobile device 300. In some embodiments, the mounting mechanism may comprise an elastic band, a clamp, a hook, a magnet, a bracket, or a holder.

The optical axis of the one or more cameras of the mobile device 300 may be aligned with one or more intraoral regions of the subject's mouth when a flange 140 of the elongated housing 110 is positioned between a tooth portion and a gum portion of the subject's mouth. The mobile device may comprise an imaging device (e.g., a camera) that can be configured to capture the one or more intraoral images or videos.

The viewing channel 150 of the elongated housing 110 may be configured to define a field of view of an intraoral region of a subject's mouth. The field of view may be sized and/or shaped to permit one or more cameras of the mobile device 300 to capture one or more videos or images of one or more intraoral regions in a subject's mouth. In some cases, the videos may comprise one or more intraoral images showing a full dental arch of the subject.

The flange 140 may be sized and shaped to couple the intraoral adapter to the subject's mouth when the flange 140 is positioned between a gum portion and a tooth portion of the subject's mouth. The intraoral adapter 100 may be suspended from the subject's mouth when the flange 140 is positioned between the gum portion and the tooth portion of the subject's mouth. The gum portion and the tooth portion may be in contact with a first side of the flange 140 and a second side of the flange 140 to support a weight of the intraoral adapter 100 when the intraoral adapter 100 is suspended from the subject's mouth. The flange 140 may be sized and shaped to permit the subject to move the intraoral adapter and/or to adjust a position or an orientation of the intraoral adapter relative to one or more intraoral regions in the subject's mouth. Adjusting the position or the orientation of the intraoral adapter relative to one or more intraoral regions in the subject's mouth may also adjust a position or an orientation of the camera of the mobile device relative to the one or more intraoral regions in the subject's mouth. Adjusting a position or an orientation of the camera of the mobile device relative to the one or more intraoral regions in the subject's mouth may further adjust a relative position and/or a relative orientation of an optical axis of the camera relative to the one or more intraoral regions in the subject's mouth. The flange 140 may remain between the gum portion and the tooth portion of the subject's mouth while the subject moves the intraoral adapter around in the subject's mouth. The flange 140 may be sized and shaped to permit the subject to capture one or more intraoral videos or images of a full dental arch of the subject. In any of the embodiments described herein, the flange 140 of the intraoral adapter may be configured to be positioned outside the field of view defined by the viewing channel of the intraoral adapter.

FIGS. 2B, 2C, 2D, and 2E illustrate another embodiment of an intraoral adapter 100 that may be used to capture intraoral videos or images. In some cases, the intraoral adapter 100 may comprise an attachment mechanism 160 for coupling a mobile device 300 to the intraoral adapter 100. The attachment mechanism 160 may comprise, for example, a strap for securing the mobile device 300 to the intraoral adapter 100. The strap may comprise a flexible and/or compliant material, such as silicone. In some cases, the strap may comprise any biocompatible material, or any material that is dishwasher safe. The strap may be adjustable to enable a user to couple various mobile devices having different sizes, shapes, and/or form factors. The adjustability of the strap may provide several advantages, including improved compatibility with different mobile devices having distinct camera configurations, or imaging sensors disposed on different portions or locations on the mobile device.

The method may permit the user to take one or more intraoral images or videos. The intraoral images or videos may be captured while the user is moving the intraoral adapter, or after the user moves the intraoral adapter to a predetermined location.

FIG. 3 illustrates a plurality of frames from intraoral videos or intraoral images that may be captured using the software application. The intraoral video may comprise a partial or full arch movement video, of which the user moved the head from left to right, right to left, up to down, or down to up. The one or more intraoral videos may be captured while the subject is biting down (i.e., when the subject's upper dental arch and lower dental arch are in contact with or adjacent to each other).

The one or more intraoral videos may be captured while the subject is not biting down completely (i.e., when at least a portion of the subject's upper dental arch and lower dental arch are not in contact with each other, or when the subject's upper dental arch and lower dental arch are separated by a separation distance).

The plurality of intraoral images may comprise a front view, a side view, a bottom view, and/or a top view of one or more portions of the subject's upper dental arch or lower dental arch. The one or more intraoral images may be captured while the subject is biting down. The plurality of intraoral images may be captured while the subject is not biting down completely. The plurality of intraoral images may comprise images of different intraoral regions within the subject's mouth.

Computer Systems

Figure 4:
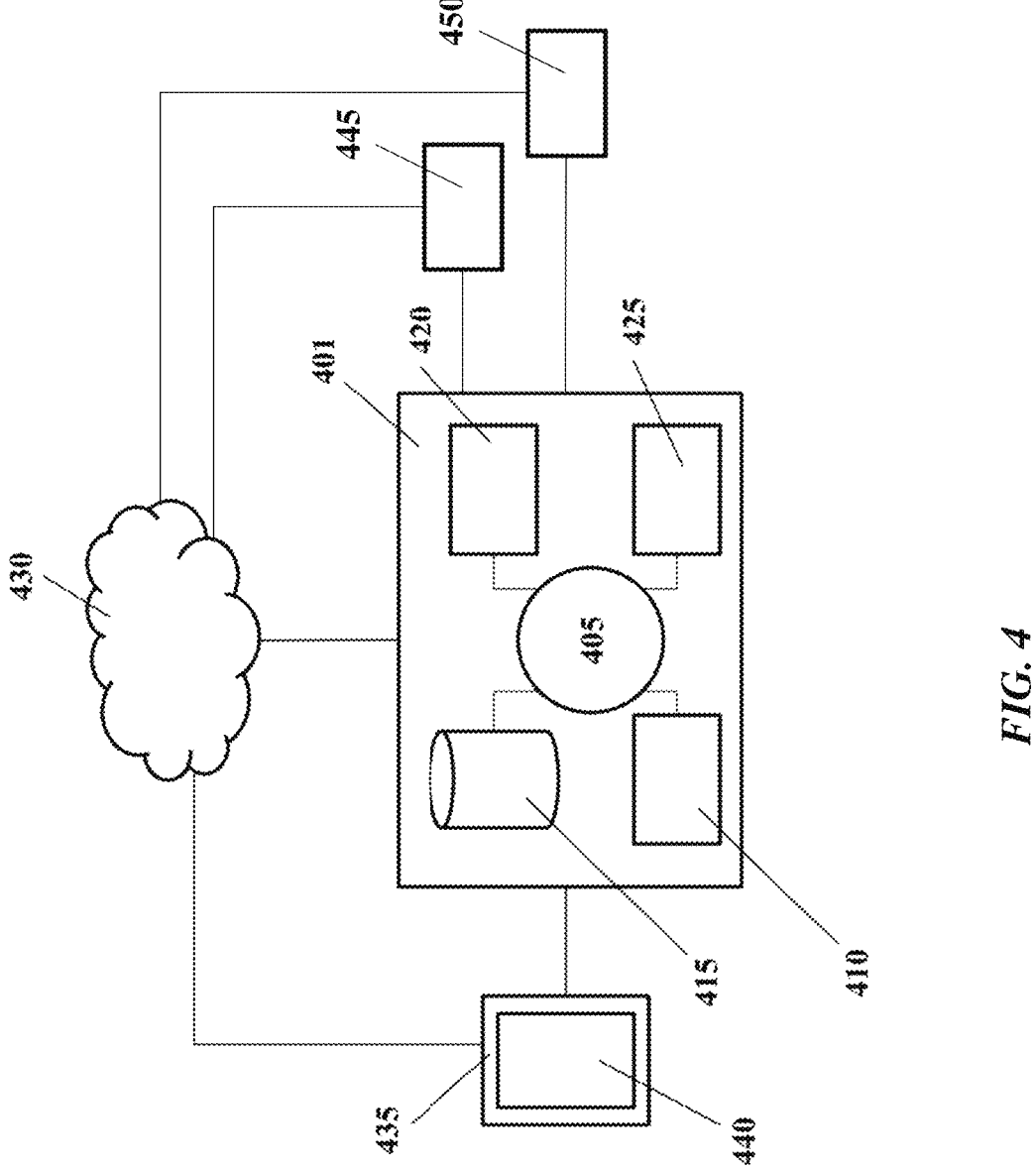
FIG. 4 schematically illustrates a computer system that is programmed or otherwise configured to implement methods provided herein, in accordance with some embodiments.

In an aspect, the present disclosure provides computer systems that are programmed or otherwise configured to implement methods of the disclosure. FIG. 4 shows a computer system 401 that is programmed or otherwise configured to implement a method for dental scan. The computer system 401 may be configured to, for example, process intraoral videos or images captured using the camera of the mobile device and determine at least one of the dental scan properties during the dental scan. The computer system 401 may be configured to, for example, process orientation or motion sensors data using the orientation or motion sensors of the mobile device and determine at least one of the dental scan properties during the dental scan. The computer system 401 may be configured to connect to a dental scan feedback device by wired connection or wireless connection. The computer system 401 may be configured to activate a dental scan feedback device to generate output. The computer system 401 can be an electronic device of a user or a computer system that is remotely located with respect to the electronic device. The electronic device can be a mobile electronic device. The computer system 401 can be a smartphone.

The computer system 401 may include a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk, Solid State drive or equivalent storage unit), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are located external to the computer system 401 (e.g., on a remote server that is in communication with the computer system 401 through an intranet or the Internet).

The computer system 401 can communicate with one or more remote computer systems through the network 430. For instance, the computer system 401 can communicate with a remote computer system of a user (e.g., a subject, a dental user, or a dentist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a storage unit. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software devices includes optical, electrical and electromagnetic waves, such as used across physical interfaces between local devices, through wired and optical landline networks and over various air-links. The physical devices that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a portal for a subject or a dental user to view one or more intraoral images or videos captured using a mobile device of the subject or the dental user. In some cases, the electronic display 435 may be the feedback device providing the generated output, for example displaying message or shape or light in accordance to some embodiments. In some cases, the user interface (UI) 440 may be the feedback device providing the generated output, for example generating sound or voice message in accordance to some embodiments. The portal may be provided through an application programming interface (API). A user or entity can also interact with various devices in the portal via the UI. Examples of UI's include, without limitation, a graphical user interface (GUI) and web-based user interface.

The computer system 401 can include or be in communication with a Camera 445 for providing, for example, ability to capture videos or images of the subject or a dental user. And for example, retrieve at least one dental scan date (such as optical object distance) that can be used to analyzed and compered to at least one dental scan properties The computer system 401 can include or be in communication with a sensor or Sensors 450 including, but not limited to orientation sensor or motion sensor for providing, for example, orientation sensor data or motion sensor data during the dental scan. And for example, retrieve at least one dental scan date (such as acceleration) that can be used to analyzed and compered to at least one dental scan properties Methods and systems of the present disclosure can be implemented by way of one or more algorithms. An algorithm can be implemented by way of software upon execution by the central processing unit 405. The algorithm can, for example, implement a method for dental scan. The method may comprise processing videos or images captured using the camera of the mobile device or processing dental scan data sensed by at least one sensor that can be used to analyze and compare to at least one dental scan properties and executed to generate output.

Dental Scan Feedback Device

Figure 5:
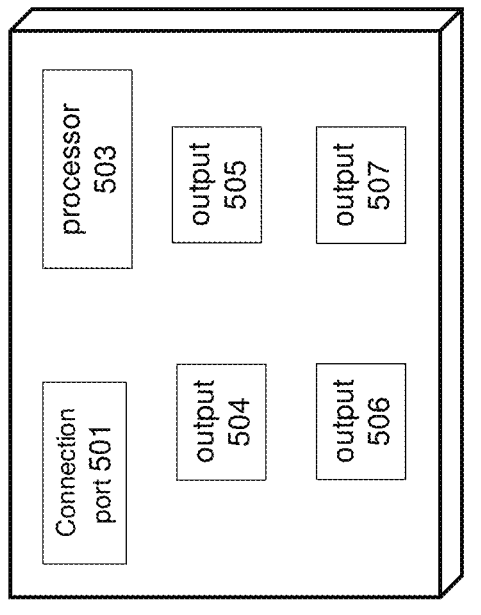
FIG. 5 schematically illustrates a dental scan feedback device comprising optional features, in accordance with some embodiments.

In an aspect, the present disclosure provides a dental scan feedback device with connection ability to a mobile device and an output means that can alert the user about dental scan properties during dental scan process. FIG. 5. provide an example of a layout of such dental scan feedback device. As shown in FIG. 5, the dental scan feedback device 50 comprises a connection port 501. The connection port can be a wired connection port or a wireless connection port and can be used to connect the dental scan mobile device to a mobile device. The mobile device can send an execution order to the dental scan feedback device 50 by the connection port 501 to generate an output by one of the output ports 504-507. The dental scan feedback device can comprise a processor 503 to process the execution order received from the mobile device and to activate one or more of the output ports 504-507.

The dental scan feedback device can comprise a speaker 504 as an output port. The feedback device output may comprise a sound, a message or a voice. The dental scan feedback device can comprise mechanical element 505 as an output port. The feedback device output may comprise a vibration, a tremble, a sound, a temperature, an electric current, a stab or a pinch. The dental scan feedback device can comprise light source 506 as an output port, and the feedback device output may comprise light. The dental scan feedback device can comprise a screen 507 as an output port, and the feedback device output may comprise a shape, a message or light showing on the screen.

FIG. 6A. illustrates an example of a dental scan feedback device that can be used during the dental scan process. The dental scan feedback device 60 can be located in front of the user during the dental scan process or can be attached to the mobile device. The dental scan feedback device 601 may comprise a connection port 603 for a wired or wireless connection to the mobile device. In some cases, a set of bulbs 602 can be LED lights. According to some embodiments, the light bulbs 602 can illuminate or change the illumination color in accordance to the progression of the dental scan process. For example, the color of the lights can change from red to green if the user conducts the dental scan process in a sufficient manner for the upper and lower arches. The dental scan feedback device 601 may comprise a speaker 604 that can produce an alert noise if the user is not keeping the dental scan properties during the dental scan process. A screen 605 can present an alert message or signs on the screen 605 if the user is not keeping the dental scan properties during the dental scan process.

FIG. 6B. illustrate an example of a dental scan feedback device that can be used during the dental scan process. The dental scan feedback device 61 can be located on the intraoral adapter 610 or can be an integrated part of the intraoral adapter that is used during the dental scan. The dental scan feedback device 610 may comprise a connection port 613 for a wired or wireless connection to the mobile device/In some cases, the dental scan feedback device 610 may comprise a set of bulbs 612. The set of bulbs 612 may be LED lights. According to some embodiments, the light bulbs 612 can illuminate or change the illumination color in accordance to the progression of the dental scan process. For example, the color of the lights can change from red to green if the user conducts the dental scan process in sufficient manner for the upper and lower arches. The dental scan feedback device 610 may comprise metal element 616 that can produce an alert, such as a low current distraction or heat to the user's lips, if the user is not keeping the dental scan properties during the dental scan process.

FIG. 6C. illustrates an example of a dental scan feedback device 62 that can be used during the dental scan process. The dental scan feedback device 620 can be a bracelet that can be worn on the user's hand during the dental scan. The dental scan feedback device 620 may comprise a connection port 623 for a wired or wireless connection to the mobile device. The dental scan feedback device 620 may comprise a set of bulbs 622. In some cases, the set of bulbs 622 are LED lights. According to some embodiments, the light bulbs 622 can illuminate or change the illumination color in accordance to the progression of the dental scan process. The dental scan feedback device 620 may comprise a metal element 626 that can produce an alert, such as a low current distraction or heat to the user's skin, if the user is not keeping the dental scan properties during the dental scan process.

While preferred embodiments of the systems and methods described herein have been shown and described herein, it will be obvious to those skilled in the art that such embodiments are provided by way of example only. It is not intended that the systems and methods described herein be limited by the specific examples provided within the specification. While the systems and methods described herein has been described with reference to the aforementioned specification, the descriptions and illustrations of the embodiments herein are not meant to be construed in a limiting sense.

Numerous variations, changes, and substitutions will now occur to those skilled in the art without departing from the systems and methods described herein. Furthermore, it shall be understood that all aspects of the systems and methods described herein are not limited to the specific depictions, configurations or relative proportions set forth herein which depend upon a variety of conditions and variables. It should be understood that various alternatives to the embodiments described herein may be employed in practicing the systems and methods described herein. It is therefore contemplated that the systems and methods described herein shall also cover any such alternatives, modifications, variations or equivalents. It is intended that the following claims define the scope of the systems and methods described herein and that methods and structures within the scope of these claims and their equivalents be covered thereby

What is claimed is:

1. A method for performing a dental scan, comprising:
(i) providing an intraoral adapter comprising (i) a viewing channel located between a proximal portion and a distal portion of an elongated housing and (ii) a mounting mechanism provided on the distal portion of the elongated housing, wherein the mounting mechanism is configured to couple the intraoral adapter to a mobile device, wherein the mobile device comprises: (a) a camera configured to capture videos or images, (b) at least one orientation sensor or at least one motion sensor, and (c) a processing unit configured to (1) process data obtained from the at least one orientation sensor or the at least one motion sensor, and (2) process a plurality of videos or images;

(ii) providing a feedback device;

(iii) coupling the intraoral adapter to the mobile device; and (iv) performing the dental scan, wherein the feedback device generates a dental scan output based on one or more dental scan properties and provides the dental scan output to a user while the user performs the dental scan.

2. The method of claim 1, wherein the mobile device is a mobile smartphone.

3. The method of claim 1, wherein the feedback device comprises a speaker, and wherein the dental scan output comprises an audio output.

4. The method of claim 1, wherein the feedback device comprises a mechanical device, and wherein the dental scan output comprises a vibration, a tremble, a sound, a temperature, an electric current, a stab, or a pinch.

5. The method of claim 1, wherein the feedback device comprises a light source, and wherein the dental scan output comprises light.

6. The method of claim 1, wherein the feedback device comprises a screen, and wherein the dental scan output comprises a shape, a message, or a light displayed on the screen.

7. The method of claim 1, wherein the one or more dental scan properties comprise at least one of: distance, direction, angle, focus, light condition, location, movement speed, motion blur, acceleration, shiver, time, tooth appearance, predetermined scan order, predetermined scan sites, dental scan properties provided by a scan administrator, specific module use, intraoral adapter coupling, or placement.

8. The method of claim 7, wherein the one or more dental scan properties further comprise reference videos or images.

9. The method of claim 8, wherein the reference videos or images are associated with one or more of: specific tooth, specific tooth angle, aligner appearance, and reference aid.

10. The method of claim 1, wherein the dental scan output alerts the user when the one or more dental scan properties are met or not met during the dental scan.

11. The method of claim 1, wherein the feedback device generates the dental scan output upon reaching at least one of the one or more dental scan properties.

12. The method of claim 1, wherein in (iv), the performed dental scan is monitored at a dispatch location, and wherein the feedback device is configured to be activated from the dispatch location to generate the dental scan output.

13. The method of claim 1, wherein the data obtained from the at least one orientation sensor or the at least one motion sensor is stored and added to the dental scan output.

14. The method of claim 1, wherein the dental scan output comprises a video.

15. A dental scan system, comprising: an intraoral adapter, a smartphone comprising a camera, and software comprising one or more dental scan properties, wherein the smartphone activates one or more features at a start, during, or at an end of an intraoral capture video to achieve the one or more dental scan properties, wherein the intraoral adapter comprises: a viewing channel located between a proximal portion and a distal portion of an elongated housing and a mounting mechanism provided on the distal portion of the elongated housing, wherein the mounting mechanism is configured to couple the intraoral adapter to the smartphone.

* * * * *